United States Patent
Pendharkar et al.

(10) Patent No.: US 7,109,163 B2
(45) Date of Patent: Sep. 19, 2006

(54) HEMOSTATIC COMPOSITIONS AND DEVICES

(75) Inventors: Sanyog M. Pendharkar, Old Bridge, NJ (US); Anne J. Gorman, Hightstown, NJ (US); Thomas L. Craven, Bridgewater, NJ (US)

(73) Assignee: Ethicon, Inc., Somerville, NJ (US)

( * ) Notice: Subject to any disclaimer, the term of this patent is extended or adjusted under 35 U.S.C. 154(b) by 94 days.

(21) Appl. No.: 10/768,912

(22) Filed: Jan. 30, 2004

(65) Prior Publication Data

US 2005/0171001 A1    Aug. 4, 2005

(51) Int. Cl.
- A01N 37/18    (2006.01)
- A01N 33/12    (2006.01)
- A61K 38/00    (2006.01)
- A61K 31/14    (2006.01)

(52) U.S. Cl. .......................... 514/2; 514/643
(58) Field of Classification Search ...................... None
See application file for complete search history.

(56) References Cited

U.S. PATENT DOCUMENTS

| | | | |
|---|---|---|---|
| 2,507,244 A | | 5/1950 | Correll et al. |
| 4,655,211 A | * | 4/1987 | Sakamoto et al. ......... 424/447 |
| 5,143,838 A | | 9/1992 | Kraus et al. |
| 5,733,572 A | | 3/1998 | Unger et al. |
| 5,908,054 A | | 6/1999 | Safabash et al. |
| 6,045,570 A | | 4/2000 | Epstein et al. |
| 6,063,061 A | | 5/2000 | Wallace et al. |
| 6,066,325 A | | 5/2000 | Wallace et al. |
| 6,566,345 B1 | | 5/2003 | Miller et al. |
| 2002/0193448 A1 | | 12/2002 | Wallace et al. |
| 2003/0028140 A1 | * | 2/2003 | Greff ......................... 604/36 |
| 2003/0064109 A1 | | 4/2003 | Qian et al. |
| 2003/0181411 A1 | * | 9/2003 | Bosch et al. ................ 514/44 |
| 2004/0101546 A1 | * | 5/2004 | Gorman et al. ............ 424/445 |
| 2004/0105889 A1 | * | 6/2004 | Ryde et al. ................. 424/489 |
| 2004/0120993 A1 | * | 6/2004 | Zhang et al. .............. 424/445 |
| 2005/0037088 A1 | * | 2/2005 | Pendharkar et al. ........ 424/490 |
| 2005/0171001 A1 | * | 8/2005 | Pendharkar et al. ........... 514/2 |

FOREIGN PATENT DOCUMENTS

| | | | |
|---|---|---|---|
| DE | 3706484 | * | 7/1988 |
| EP | 0740528 B1 | | 11/1994 |
| EP | 0927053 B1 | | 4/2003 |
| JP | 62226009 A | | 10/1987 |
| WO | WO 98/08550 A1 | | 3/1998 |
| WO | WO 00/78533 A1 | | 12/2000 |
| WO | WO 01/97826 A2 | | 12/2001 |
| WO | WO 1/97873 A2 | | 12/2001 |
| WO | WO 02/072128 A1 | | 9/2002 |
| WO | WO 03/007845 A1 | | 1/2003 |
| WO | WO 03/055531 A2 | | 7/2003 |
| WO | WO 2005/016256 A | | 2/2005 |
| WO | WO 2005/016257 A | | 2/2005 |

OTHER PUBLICATIONS

Wikipedia, the free encyclopedia. Benzalkonium Chloride. http://en.wikipedia.org/wiki/Benzalkonium_chloride (accessed online Oct. 6, 2005).*
Oie et al. Microbial Contamination of In-use Lubricants for Non-touch Urethral Catheters in Intermittent Self-catheterization. Biol. Pharm. Bull. 2000. vol. 23, No. 6, pp. 781-783.*
International Search Report dated Dec. 12, 2005 for corresponding Appln. No. PCT/US04/23779.
Sakurabayashi, "Clinical Evaluation of New Hemostatic Agent for Hemostasis from Biopsy Wounds in the Liver", Gastroenterological Endoscopy, vol. 30 (10), ( )ct. 1988), pp. 2256.
European Search Report dated Jun. 10, 2006 for corresponding Appln. No. EP 06260487.

* cited by examiner

*Primary Examiner*—Bruce R. Campell
*Assistant Examiner*—Marcela M Cordero Garcia

(57) ABSTRACT

The present invention includes both sterilized and unsterilized hemostatic compositions that contain a biocompatible liquid having particles of a biocompatible polymer suitable for use in hemostasis and which is substantially insoluble in the liquid, up to about 20 percent by weight of glycerol and about 1 percent by weight of benzalkonium chloride, each based on the weight of the liquid, all of which are substantially homogenously dispersed throughout the liquid to form a substantially homogenous composition, methods for making such compositions, medical devices that contain such hemostatic compositions disposed therein and methods of making such devices.

22 Claims, No Drawings

HEMOSTATIC COMPOSITIONS AND DEVICES

FIELD OF THE INVENTION

The present invention relates to flowable hemostatic compositions suitable for use in hemostatic devices that are suitable for applying a flowable hemostatic composition to a site requiring hemostasis, to such hemostatic devices utilizing such compositions and to methods of making such compositions and devices.

BACKGROUND OF THE INVENTION

Gelatin-based hemostats, both in solid sponge or powder form, are commercially available and are used in surgical procedures. Gelatin powder, when mixed with fluid, can form a paste or slurry that is useful as a flowable, extrudable and injectable hemostat for diffuse bleeding, particularly from uneven surfaces or hard to reach areas. The conventional slurry is prepared at the point of use by mechanical agitation and mixing of the powder and liquid to provide uniformity of the composition. The paste then is placed into a delivery means or applicator, e.g. a syringe, and applied to the wound.

The main disadvantage of this approach is the need to mix the powder with the liquid, knead it into a paste and back-fill it into the delivery device of choice, all at the time of need and at the point of use. The manipulations are time consuming and potentially can compromise the sterility of the delivered product. Thus, a need exists for a sterile, flowable, moldable hemostatic composition that is ready to use at the point of use or can be prepared with minimal manipulation and without risk of compromising the sterility of the product.

It would be desirable if a hemostatic device, e.g. a delivery means such as a syringe or other applicator, would be pre-filled with a hemostatic composition and instantly available to the surgeon at the point of use without need for further manipulation. The hemostatic composition pre-filled in the device or applicator should be sterile and flowable and should require minimum preparation time and minimal force when extruded or injected through the delivery means at the point of use. The compositions of the present invention provide such properties and pre-filled devices.

SUMMARY OF THE INVENTION

The present invention is directed to hemostatic compositions suitable for use in preparing hemostatic devices for applying a flowable hemostatic composition to a site requiring hemostasis. The composition comprises a substantially homogenous paste, or slurry, containing a biocompatible liquid, solid, porous or non-porous particles of a biocompatible polymer suitable for use in hemostasis and which are substantially insoluble in the liquid, up to about 20 weight percent of glycerol, based on the weight of the liquid, and up to about 1 weight percent of benzalkonium chloride, based on the weight of liquid. The solid particles, glycerol and benzalkonium chloride are substantially homogenously dispersed throughout the liquid. The ratio of the liquid to the solid particles is effective to provide the composition with hemostatic properties, both prior to and after sterilization. Compositions of the present invention may be prepared well in advance of the time of use and need not be prepared at the point of use, yet they maintain physical properties effective to provide flowability, extrudability or injectability at the point and time of use. The present invention also includes methods of making the hemostatic compositions, medical devices containing the sterilized compositions disposed therein and methods of making such devices.

DETAILED DESCRIPTION OF THE INVENTION

Both sterilized and unsterilized compositions of the present invention contain solid, porous or non-porous particles of a biocompatible polymer suitable for use in hemostasis, a biocompatible liquid, glycerol and benzalkonium chloride. The components of the compositions are combined and mixed under conditions effective to provide a substantially homogeneous hemostatic composition. The amount and average diameter of particles contained in the composition and the relative amounts of the solid and liquid is effective to provide the composition with hemostatic and physical properties, as described herein below.

The hemostatic composition so formed is a hemostatic paste, or slurry, that exhibits improved properties when compared to pastes that do not contain benzalkonium chloride and glycerol. Compositions of the present invention may be prepared, filled into a medical device, such as a syringe or other known applicators used to dispense conventional hemostatic compositions, and sterilized by ionizing irradiation, well in advance of the time of their intended use. The compositions further may include additives to facilitate the preparation of the composition, enhance physical and mechanical properties, enhance the hemostatic properties of the composition and provide antimicrobial properties.

As used herein, "substantially homogenous" denotes that physical state of the compositions or pastes where the solid is uniformly dispersed throughout the liquid such that the ratio of solid: liquid is substantially the same.

As used herein, "sterile" means substantially free of living germs and/or microorganisms and as further recognized and described by governmental standards pertaining to compositions and medical devices described and claimed herein.

As used herein, "hemostatic", or "hemostatic properties", means the ability to stop or minimize bleeding, as one skilled in the art of hemostasis would understand those terms to mean, as further exemplified in the examples of the specification and as further recognized and described by governmental standards pertaining to compositions and medical devices described and claimed herein.

As used herein, "Peak Expression Force" is the peak force value required to extrude compositions from a pre-filled 10 cc Becton Dickinson (BD) luer syringe fitted with a 14 gauge angiocatheter tip, as described in the examples of the specification.

A variety of biocompatible natural, semi-synthetic or synthetic polymers may be used to prepare the solid particles used in compositions of the present invention. The polymer selected must be substantially insoluble in the liquid chosen for the particular composition. Preferably, water-insoluble biodegradable polymers that provide mechanical, chemical and/or biological hemostatic activity are used. Polymers that may be used include, without limitation, proteins and polysaccharides. Polysaccharides that may be used include oxidized cellulose, chitosan, chitin, alginate, oxidized alginate and oxidized starch. The biocompatible polymer used to prepare the particles preferably is a cross-linked or denatured protein, such as gelatin, collagen, fibrinogen or fibronectin. A preferred gelatin powder is Surgifoam® hemostatic gelatin powder, available from Johnson &

Johnson Wound Management, a division of Ethicon, Inc. Surgifoam® powder is a partially cross-linked gelatin powder prepared by milling gelatin sponge into particles having an average diameter of from about 40 microns to about 1200 microns, more preferably from about 100 microns to about 1000 microns, as determined by laser diffraction.

Composition of the present invention comprises a continuous liquid phase in which the solid particles, glycerol and benzalkonium chloride are dispersed. Depending upon the particular medical device and use thereof, the liquid may be aqueous or non-aqueous. Preferably, the liquid is aqueous. Aqueous liquids may include, without limitation, biocompatible aqueous solutions, such as calcium chloride and saline. More preferably, the liquid comprises saline. The liquid and solid particles are present in relative amounts effective to provide a paste, or slurry, suitable for use in providing hemostasis. Excessive dilution of the solid particulate phase, although beneficial to further reduce the peak value expression force, will detrimentally affect the hemostatic properties of the material and therefore is not desired. The weight ratio of solid particles to liquid generally is from about 1:2 to about 1:12. A preferred weight ratio of the solid gelatin particles to saline is from about 1:3 to about 1:6.

Compositions of the present invention include compositions described herein that are sterile, in that they have been irradiated with ionizing irradiation. Such irradiation may include e-beam or gamma irradiation. The level of irradiation and conditions of sterilization, including the time that the compositions are irradiated, are those that provide sterile compositions, as defined herein. Once having the benefit of this disclosure, one skilled in the art will be able to readily determine the level of irradiation necessary to provide sterile compositions.

Glycerol is added to the compositions of the invention to enhance the extrudability or injectability of the composition. Glycerol is present in the compositions at from about 0% to about 20% by weight of the liquid. Preferably, the composition comprises from about 1% to about 10% by weight of glycerol, based on the weight of the liquid. More preferably, the compositions comprises from about 1% to about 5% by weight of glycerol, based on the weight of the liquid.

In addition, quaternary amines, such as benzalkonium chloride, Polybrene or Onamer M are used to provide enhanced properties to the compositions. Preferably, benzalkonium chloride is used at levels up to about 1 percent by weight of the compositions, based on the weight of the liquid. More preferably, benzalkonium chloride is used at levels of from about 0.001% to about 0.01% by weight of the compositions, based on the weight of the liquid. Even more preferably, the compositions comprise from about 0.002 to about 0.006% by weight benzalkonium chloride, based on the weight of the liquid. It is believed that the benzalkonium chloride serves multiple functions in the compositions, acting as an antimicrobial agent, a foaming agent, a radical scavenger and as a heparin neutralizer.

Such hemostatic compositions may further comprise heparin neutralizers, procoagulants or hemostatic agents, such as thrombin, fibrinogen, fibrin, Factor Xa, or Factor VIIa. By "effective amount", it is meant that amount necessary to provide to the compositions those properties for which the additive is being added. The effective amount also is limited by the maximum amount that may be added without causing detrimental biological affects.

Compositions of the present invention are particularly advantageous for use in hemostatic compositions where additives that are sensitive to irradiation are utilized. For example, thrombin, in an aqueous solution, has been found to lose all procoagulant activity when exposed to sterilization irradiation. In contrast, thrombin retained approximately 40% of its original enzymatic activity and all of its hemostatic activity after sterilization when formulated in compositions according to this invention, as shown in Example 3. While bovine thrombin is exemplified herein, human-derived thrombin also may be used in compositions of the present invention.

Medical devices in which the hemostatic compositions of the present invention may be utilized include any device currently being used to apply a flowable or injectable hemostatic paste or slurry to a site, or wound, requiring hemostasis. The site requiring hemostasis may be the result of an injury or a surgical procedure. Examples of devices or applicators include syringes such as Becton Dickinson luer or Monoject syringes. Other devices are disclosed in detail in U.S. Pat. No. 6,045,570, the contents of which are incorporated by reference in their entirety.

In one embodiment for making compositions of the invention, a substantially homogenous paste is prepared by first mixing the benzalkonium chloride and glycerol in saline to form a solution. The saline solution may include effective amounts of other additives dissolved therein as described above. The particles then are incorporated into the solution by mixing until they are substantially homogenously dispersed throughout the liquid, thus providing the substantially homogenous paste, or slurry. Mixing may be accomplished by extrusion or by mixing in a confined space under conditions effective to provide a uniform dispersion of the solid particles and in the solution. A preferred ratio (w/v) of solid particles to liquid is from about 1:12 to about 1:2 (g/ml).

Alternately, a double planetary mixer may be utilized in making compositions of the present invention. The saline solution is prepared as above and added to the mixer. The solid particles, most commonly in the form of a powder, then are added to the solution in the mixer over time with continuous mixing until such time as a substantially homogenous composition is formed containing the solid particles and uniformly dispersed throughout the solution. If desired, the powder may be compacted or compressed prior to addition to the solution to improve handling and to minimize dust; provided that, the porosity or diameter of the particles in and of themselves is not affected.

The hemostatic compositions prepared as above are transferred into a medical device as described above and the device containing the hemostatic composition is sterilized, preferably by ionizing radiation. More preferably, sterilization is by gamma irradiation as exemplified herein.

While the following examples demonstrate certain embodiments of the invention, they are not to be interpreted as limiting the scope of the invention, but rather as contributing to a complete description of the invention.

EXAMPLES

Example 1

A total of ten samples were prepared as follows. 1 gram of dry Surgifoam® powder was placed in a plastic container and mixed with 4 ml of saline. The container was capped and the contents were shaken until a substantially homogenous paste of uniform consistency was obtained. The paste was formed into a cylindrical shape and placed into a 10 cc BD polypropylene disposable luer syringe. The syringes were then capped and five of the filled syringes were sterilized by gamma irradiation at a dose of 25 kGy. The Peak Expression Force was determined and presented in Table 1. Unsterilized samples are designated as 1a and sterilized samples are designated as 1b.

Example 2

A total of ten samples were prepared as follows. A saline solution containing 0.005% by weight of benzalkonium chloride and 5% by weight of glycerol was prepared. This solution was used to prepare homogenous gelatin-powder pastes as described in Example 1. The paste was formed into a cylindrical shape and placed into a 10 cc BD polypropylene disposable luer syringe. The syringes were then capped and five of the filled syringes were sterilized by irradiation at a dose of 25 kGy. The Peak Expression Force was determined and presented in Table 1. Unsterilized samples are designated as 2a and sterilized samples are designated as 2b.

Peak Expression Force Determination:

Samples prepared in the Examples below were tested for peak expression force as determined using a Chatillon TCD 200, using a 50-lb load cell [DFG 550] at a speed of 2 inches/min. An in-dwelling catheter sheath (size 12–14 gauge) was attached to the sample syringe to be tested. The syringe then was inserted into a holding apparatus, which then was loaded onto the test instrument. The peak expression force was noted.

TABLE 1

| Samples | Peak Expression Force lbs (n = 5) |
|---|---|
| Samples 1a | 21.8 |
| Samples 1b | 26.4 |
| Samples 2a | 17.2 |
| Samples 2b | 22.4 |

As the data in Table 1 indicates, the inclusion of the glycerol and benzalkonium chloride homogenously dispersed throughout the paste significantly reduces the peak expression force of the composition prior to sterilization compared to pastes that do not include the glycerol and benzalkonium chloride. Consequently, the sterilized composition of the present invention exhibits a peak expression force significantly less than that of a sterilized paste that does not include these components. In fact, the peak expression force of the sterilized composition of the present invention approximates the peak expression force of the pre-sterilized paste containing no glycerol or benzalkonium chloride.

Hemostatic performance of different materials in porcine splenic biopsy punch model:

A porcine spleen biopsy punch model was used for evaluation of the hemostatic properties of samples prepared in Examples 1 and 2. A 6-mm biopsy punch was used to cut a tissue flap 3 mm deep. The tissue flap was cut out and 0.4 ml of the test materials was applied to the wound site. Manual compression was held over the wound site for 2 minutes. The wound site was then observed for up to 3 minutes for signs of bleeding. If additional bleeding was observed, additional applications of manual compression for 30 seconds each time were used until complete hemostasis was achieved. Table 2 lists the results of the evaluation. Results for unsterilized or sterilized samples are represented as an average values for all samples tested.

TABLE 2

In vivo Hemostasis Performance

| Samples | Number of Compressions | Time to Hemostasis (mins:seconds) |
|---|---|---|
| Samples 1a | 3 | 3:35 (n = 2) |
| Samples 2a | 3 | 3:33 (n = 2) |
| Samples 1b | 1 | 2:00 (n = 3) |
| Samples 2b | 2 | 3:00 (n = 6) |

Example 3

Two vials of lyophilized Bovine thrombin (20,000 units Thrombogen JJMI) were reconstituted in 20 ml of saline to provide a working solution of 1000 u/ml. Clotting activity was measured in an in vitro test as described in Example 3. One vial of this material was stored at 4–8° C. and the clotting activity measured at day 1, day 8 and day 30, respectively. The second vial was sterilized by gamma irradiation (25 kGy) and the clotting activity measured as below. The unsterilized and sterilized samples were designated samples 3a and 3b, respectively. Both sterilized and unsterilized samples were stored at 4–8° C. between measurements.

Another 2 vials of 20,000 units of lyophilized bovine thrombin were reconstituted in saline containing 0.005% benzalkonium chloride and 5% glycerol.

One vial was stored at. 4–8° C. and the clotting activity was measured at day 0, day 1, day 8 and day 30. The second vial was sterilized by gamma irradiation (25kGy) and the clotting activity measured as below. In between measurements both the sterilized and unsterilized samples were stored at 4–8° C. The unsterilized and sterilized samples were designated samples 3c and 3d, respectively.

Gelatin pastes containing the thrombin noted above were prepared by mixing 1 gram of Surgifoam gelatin powder with 5 ml of thrombin solution as described above. Sample 3e was prepared by mixing Surgifoam powder with 5 ml of the unsterilized solution of sample 3c. The resulting pastes were loaded into 10cc syringes. The syringes then were sterilized by gamma irradiation (25kGy) and the clotting activity measured as below.

Measurement of Thrombin activity by an in vitro coagulation test in a Fibrometer instrument (BBL)

Method:

Serial dilutions of test sample containing thrombin were prepared in Veronal buffer pH 7.2. 0.2 ml of pooled normal plasma (Citrol Level 1 control plasma-Dade Diagnostics) was warmed to 37° C. in the fibrometer incubator block. 0.1 ml of sample dilution was added to the plasma and the timer started simultaneously. The time to clot formation was recorded. All samples were tested in duplicate and an average clotting time calculated. Data was graphed as the $log_{10}$ dilution vs. $log_{10}$ clotting time and a regression analysis performed. Freshly prepared thrombin was considered to have 100% activity and all other samples were calculated as a percentage of the activity relative to the freshly prepared thrombin. Results are presented in Tables 3 and 4.

TABLE 3

Effect of Storage time on Thrombin Activity:
Stabilization by Formulated Gelatin Paste

| Storage Solution | Percent Loss in Thrombin Activity | | | |
|---|---|---|---|---|
| (Stored at 6° C.) | Time 0 | Day 1 | Day 8 | Day 30 |
| 3a | 0 | 0 | 53.3 | 90.8 |
| 3c | 0 | NA | 41.1 | 82.9 |
| 3g | 0 | 0 | 0.8 | 0 |

TABLE 4

Effect of Gamma Irradiation on Thrombin Activity:
Stabilization by Formulated Gelatin paste

| Media for Sterilized Thrombin * Samples (5 ml/g gelatin powder-25 kGy Dose) | % Loss in Thrombin Activity Day 6 |
|---|---|
| 3b | 100 |
| 3d | 96.0 |
| 3e | 72.6 |
| 3h | 79.2 |

We claim:

1. A hemostatic composition, comprising:
   a biocompatible liquid,
   particles of a biocompatible polymer suitable for use in hemostasis and which is insoluble in said liquid,
   from 0.001 to about 1 percent by weight of said liquid of benzalkonium chloride; and
   up to about 20 percent by weight of said liquid of glycerol, wherein said particles, glycerol and benzalkonium chloride are substantially homogenously dispersed through said liquid, and wherein the ratio of said liquid to said particles is effective to provide said composition with hemostatic properties and a peak expression force of no greater than 22.4.

2. The composition of claim 1 wherein said liquid is aqueous.

3. The composition of claim 2 wherein said liquid comprises saline.

4. The composition of claim 3 wherein said biocompatible polymer is a protein selected from the group consisting of gelatin, collagen, fibrinogen and fibronectin.

5. The composition of claim 4 wherein said protein comprises gelatin.

6. The composition of claim 5 wherein the average diameter of said particles is from about 40 to about 1200 microns.

7. The composition of claim 6 wherein said particles and said liquid are present in said hemostatic composition at a ratio of from about 1:2 to about 1:12, based on g:ml.

8. The composition of claim 1 further comprising a functionally effective amount of an additive selected from the group consisting of antimicrobial agents, foaming agents, foam stabilizers, surfactants, antioxidants, humectants, thickeners, diluents, lubricants, wetting agents, irradiation stabilizers, plasticizers, heparin neutralizers, procoagulants and hemostatic agents.

9. The composition of claim 1 comprising from about 1 to about 10 weight percent of glycerol, based on the weight of liquid.

10. The composition of claim 1 comprising from about 0.001 to about 0.01 weight percent of glycerol, based on the weight of liquid.

11. The composition of claim 1 wherein said composition is sterile.

12. The composition of claim 8 wherein said composition is sterile.

13. The composition of claim 12 wherein said functional additive is selected from the group consisting of fibrinogen and thrombin.

14. A method for making the homogenous hemostatic composition of claim 1, said method comprising:
   preparing a solution comprising a biocompatible liquid containing up to about 20 weight percent glycerol and up to about 1 percent benzalkonium chloride, based on the weight of said liquid,
   combining said solution with particles of a biocompatible polymer suitable for use in hemostasis and which is substantially insoluble in said solution; and
   mixing said solution and said particles under conditions effective to substantially homogeneous disperse said particles throughout said solution, thereby forming said substantially homogeneous hemostatic composition,
   wherein the ratio of said liquid to said particles is effective to provide said composition with hemostatic properties.

15. The method of claim 14 wherein said liquid comprises saline.

16. The method of claim 15 wherein said biocompatible polymer is a protein selected from the group consisting of gelatin, collagen, fibrinogen and fibronectin.

17. The method of claim 16 wherein said protein comprises gelatin.

18. The method of claim 17 wherein the average diameter of said particle is from about 40 to about 1200 microns.

19. The method of claim 14 further comprising adding to said liquid a functionally effective amount of an additive selected from the group consisting of antimicrobial agents, foaming agents, foam stabilizers, surfactants, antioxidants, humectants, lubricants, thickeners, diluents, wetting agents, irradiation stabilizers, heparin neutralizers, procoagulants and hemostatic agents.

20. The method of claim 14 further comprising irradiating said substantially homogeneous composition with an amount of ionizing irradiation and for a time effective to provide a sterile, substantially homogeneous composition.

21. The method of claim 19 further comprising irradiating said substantially homogeneous composition with an amount of ionizing irradiation and for a time effective to provide a sterile, substantially homogeneous composition.

22. The method of claim 21 wherein said additive is selected from the group consisting of fibrinogen and thrombin.

* * * * *